US011234099B2

(12) United States Patent
Roy et al.

(10) Patent No.: US 11,234,099 B2
(45) Date of Patent: *Jan. 25, 2022

(54) WIRELESS LOCATION RECOGNITION FOR WEARABLE DEVICE

(71) Applicant: KONINKLIJKE PHILIPS N.V., Eindhoven (NL)

(72) Inventors: Prasenjit Roy, Northborough, MA (US); Tomas Russ, Chelmsford, MA (US); Chibing Liu, Boston, MA (US); Paul Baril, Boylston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/441,403

(22) Filed: Jun. 14, 2019

(65) Prior Publication Data

US 2019/0297460 A1  Sep. 26, 2019

Related U.S. Application Data

(63) Continuation of application No. 15/789,314, filed on Oct. 20, 2017, now Pat. No. 10,327,103.

(51) Int. Cl.
*H04M 11/04* (2006.01)
*H04W 4/02* (2018.01)
(Continued)

(52) U.S. Cl.
CPC .......... *H04W 4/023* (2013.01); *A61B 5/0022* (2013.01); *G01S 5/02* (2013.01); *G01S 19/17* (2013.01);
(Continued)

(58) Field of Classification Search
CPC ....... H04W 4/02; H04W 4/024; H04W 4/029; H04W 64/00; H04W 76/50; H04W 36/18;
(Continued)

(56) References Cited

U.S. PATENT DOCUMENTS 9,253,605 B2   2/2016   Alizadeh-Shabdiz
9,402,154 B2   7/2016   Houri
(Continued)

FOREIGN PATENT DOCUMENTS

FR       2915343 A1    10/2008
WO    2010015854 A1     2/2010
(Continued)

OTHER PUBLICATIONS

"MPERS Wearables:Benefits of Hybrid Location for the Emergency Device"; Downloaded From http:www.skyhookwireless.com/blog/devices/wearables/mpers-wearables-benefits, Skyhook Wireless, NC, 2016, 7 Page Document.

*Primary Examiner* — Huy C Ho (57) ABSTRACT

In one embodiment, an apparatus (12) is presented that detects wireless signals from external devices (18) that uniquely identify each of the external devices, records, in memory (30), information about the external devices without access to an external database, and compares information from the external devices to determine a relative location of the wearable device without using additional, power-hungry position location functionality if there is a threshold match in the compared information. In some embodiments, the invention uses the determined relative location to trigger an action at another device. The invention, using self-contained functionality, enables improvements in same location or home location determination accuracy, memory conservation, and power consumption.

11 Claims, 6 Drawing Sheets

(51) Int. Cl.
*A61B 5/00* (2006.01)
*G01S 5/02* (2010.01)
*G01S 19/17* (2010.01)
*G01S 19/34* (2010.01)
*G08B 21/02* (2006.01)
*G08B 25/01* (2006.01)
*H04W 4/90* (2018.01)

(52) U.S. Cl.
CPC .............. *G01S 19/34* (2013.01); *G08B 21/02* (2013.01); *G08B 25/016* (2013.01); *H04W 4/90* (2018.02)

(58) Field of Classification Search
CPC ..... H04W 36/30; H04W 36/34; H04W 36/36; H04W 36/365; H04W 36/38; H04W 36/385; H04W 48/20; H04W 16/32; H04W 88/08; H04W 88/10; H04W 4/90; H04W 4/023; G01S 19/17; G01S 19/34; G01S 5/02; G08B 21/02; G08B 25/016; A61B 5/0022; A61B 5/1112; A61B 5/6898; A61B 5/0205; A61B 5/1117

USPC ...................................................... 455/404.2
See application file for complete search history.

(56) References Cited

U.S. PATENT DOCUMENTS

| | | |
|---|---|---|
| 2008/0224925 A1 | 9/2008 | Ochenbauer |
| 2010/0285815 A1 | 11/2010 | Treu et al. |
| 2012/0268249 A1 | 10/2012 | Kansal et al. |
| 2013/0303186 A1* | 11/2013 | Gordon ................ H04W 64/00 455/456.1 |
| 2015/0097670 A1 | 4/2015 | Chitre et al. |
| 2016/0094953 A1* | 3/2016 | Russ ..................... H04W 76/50 455/404.2 |
| 2018/0103859 A1* | 4/2018 | Provenzano ......... A61B 5/0816 |

FOREIGN PATENT DOCUMENTS

| | | |
|---|---|---|
| WO | 2013093785 A1 | 6/2013 |
| WO | 2013166595 A1 | 11/2013 |

* cited by examiner

WIRELESS LOCATION RECOGNITION FOR WEARABLE DEVICE

CROSS-REFERENCE TO PRIOR APPLICATIONS

This application claims the benefit of, and is a continuation of, co-pending U.S. application Ser. No. 15/789,314, filed on Oct. 20, 2017 which is hereby incorporated by reference in its entirety herein.

FIELD OF THE INVENTION

The present invention is generally related to a mobile communications device, and in particular, wireless location recognition functionality for such a device.

BACKGROUND OF THE INVENTION

Wearable devices used for enabling a user to communicate a request for help (e.g., to an emergency call center, family member, etc.) in the event of an emergency, sometimes referred to as mobile personal emergency response system (MPERS) devices, tend to be small in size with a limited battery capacity. Elderly users often use the MPERS devices with position location functionality (e.g., Global Positioning System or GPS) to assist others in determining their location, particularly when the user is rendered unconscious or is mentally incapacitated from, say, a fall event or deteriorating medical condition, respectively. However, obtaining a location fix via a GPS operation is very power consuming, thus requiring the user to re-charge the battery frequently. Further, for emergencies at home, often times a GPS signal is not available, so when an alarm is communicated to, for instance, a PERS service center, personnel at the service center may be unable to accurately locate the MPERS device (e.g., to confirm the location for the emergency event is a home location for the user).

In an on-line article entitled, "MPERS Wearables: Benefits of Hybrid Location for the Emergencies Device," posted by Ashley Osgood on Jun. 10, 2014, the article describes traditional MPERS devices worn as pendants or bracelets, which transmit an alert from the wearer to a base unit nearby (usually within the home). The base unit, in turn, dispatches an alert to a central location. The article goes on to describe how advances to MPERS devices includes the ability to automatically detect a fall based on motion patterns, with the industry transitioning from requiring the wearer to be tied to one place in order to assure constant transmission of location data from the stationary location within their home to now being much more mobile, fast, and accurate. To achieve the features desired in the article, the article informs of hybrid location functionality for such devices, and which combine Wi-Fi positioning with GPS, cell tower, IP, and device sensor data. However, with the increased functionality comes the need for improvements in power conservation and/or memory usage.

SUMMARY OF THE INVENTION

One object of the present invention is to develop an apparatus that is self-contained in its ability to recognize a relative location in an energy efficient manner. To better address such concerns, in a first aspect of the invention, an apparatus is presented that detects wireless signals from external devices that uniquely identify each of the external devices, records, in memory, information about the external devices without access to an external database, and compares information from the external devices to determine a relative location of the apparatus without using additional, power-hungry position location functionality if there is a threshold match in the compared information. The invention, using self-contained functionality, enables improvements in location determination accuracy, memory conservation, and power consumption.

In one embodiment, a processor of the apparatus is further configured to run executable code to receive a command from a remote location based on a trigger, the trigger comprising transmittal of an alert. The command may comprise a set home location command sent by a device of an agent at a personal emergency response system (PERS) facility that is triggered by the alert that is transmitted by the apparatus, enabling a confirmation by an agent of the user's home location.

In one embodiment, the processor is configured to run the executable code to further detect an emergency event for a user possessing the apparatus, and based on the detection, cause the transmittal of the alert. The apparatus serves to assist the user in the case of an emergency event, whereby the alert may prompt assistance from emergency responders or designated caregivers.

In one embodiment, the alert further comprises the same location or the location from the location fix. The location may be that determined from a wireless scan, or if there is no match, that according to the location fix, thus providing an agent at the PERS facility with an accurate location to enable a quick and possibly life-saving response, yet determined in an efficient manner to preserve the power of the battery operated apparatus.

In one embodiment, the processor is configured to run the executable code to cause the wireless communications module to perform another wireless scan. This operation is part of the set home location command delivered from the PERS facility, and serves to further establish an accurate record of the home location for a user, which of course may vary over the course of time. The wireless scan is performed in part to obtain information (e.g., identifier information, signal strength, etc.) from the nearby external devices.

In one embodiment, the processor is configured to run the executable code to associate external devices detected from the another wireless scan to a home location. The external devices, which may be Wi-Fi access points or wireless devices that transmit signals of other standards, specifications, or that transmit signals of other ranges of the electromagnetic spectrum, are detected from the wireless scan and associated with the home location. In some embodiments, only a predetermined (e.g., as configured by a user or the manufacturer of the apparatus) quantity of the external devices revealed by the wireless scan are associated with (e.g., as indicated by a bit setting or coding in memory) the home location. In some embodiments, all of the detected external devices are used in association with the home location.

In one embodiment, the association of the location of the apparatus to the home location is achieved without a location fix from the position location module. By performing the wireless scan without implementing a location fix, the set home location operation is achieved accurately and quickly using a reduced power footprint.

In one embodiment, wherein responsive to the threshold match, the processor is configured to run the executable code to further update a time stamp in memory corresponding to the information for the first set of external devices without populating the memory with the information for the second set of external devices. This makes efficient use of memory, eliminating the need to populate the memory with information from each scan. Further, when the record of the scans are presented as part of an alert, the agent at the PERS facility has a more comprehensive record of where the user is located, whereas if the memory was overwritten by the same location data (e.g., if the user remained at home for an extended period of time), in the event of a fall, the record may merely be a repeat of the information from the same external devices.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Disclosed herein are certain embodiments of a mobile, personal emergency response system (MPERS) device and method that make use of nearby external devices (e.g., wireless fidelity (Wi-Fi) access points (APs), Bluetooth-enabled devices, Internet-of-things devices, etc.) to save battery power by recognizing the MPERS device as being at a same location, or further identifying the MPERS device being at a home location, so as to shut off (e.g., power down to a sleep mode or turn off power to the component) a routine location positioning operation (e.g., GPS location fix or cell tower triangulation). Functionality for home location recognition may also enhance the MPERS device's locating performance/speed during, for instance, transmittal of alarms, since when a GPS fix is not available at home, a personal emergency response system (PERS) service center is able to determine the device relative location quickly (e.g., the home location) without going through a further locating process.

In one embodiment, during periodical Wi-Fi scanning, the MPERS device stores/records information about the external devices (e.g., nearby APs) in its memory without the need for access to an external database (such as to copy an external database to memory), and compares information from a current scan with information of APs from the previous record to determine if there is a threshold match. If there is a threshold match, then a same location for the MPERS device is recognized. Furthermore, when an alarm from the home is processed (e.g., where an emergency event is detected by the MPERS device, triggering an alarm), PERS service staff may send a set home location command (e.g., over the air), which instructs the MPERS device to (automatically) perform a Wi-Fi scan and to store the Wi-Fi APs for the home location (as designated or associated via recognition of access points from a scan) in the MPERS device. If later Wi-Fi APs, detected in a Wi-Fi scan according to a routine Intelligent Bread Crumbing (IBC) operation (explained further below), matches the home location, the MPERS device does not need to obtain a GPS fix or Wi-Fi location with an external database and does not need to store a duplicate location record. Rather, certain embodiments of an MPERS device update a last home/location timestamp, and this last home/location timestamp will be reported to the PERS service center when the device is reporting an alarm. This functionality helps to track down the user when currently there is no GPS fix available. When the MPERS device detects a mismatch of Wi-Fi APs of a home location or same location, the device resumes the regular IBC routine that includes both the Wi-Fi scanning and a GPS location fix.

Low battery consumption is important to MPERS devices, among other wearables or portable devices, such that conservation of power mitigates the need for users to frequently recharge the devices. Accurate and fast locating is also important for the MPERS devices to report the emergency location. By skipping the GPS functionality when not needed (e.g., when there is a threshold match of information between a current and prior wireless scan), certain embodiments of a MPERS device provide for several improvements over the state of the art. For instance, skipping the GPS functionality lowers the battery power consumption, which avoids frequent battery re-charge for the MPERS device. Also, in indoor environments, the GPS signal may either be unavailable or very weak, preventing a GPS fix during, say, an emergency event that triggers an alarm. Even inside a home or the same building, MPERS device users may move to some locations that have a weak or no Wi-Fi signal, which though providing a hindrance to location determination (i.e., if weak Wi-Fi signal) for the MPERS device of the present disclosure, compared to conventional techniques, still performs better in terms of power savings and/or response times. Therefore, same location recognition and home location recognition effectively provides a service agent the latest known location, so as to provide the best service to the MPERS users (e.g., subscribers). Further, sometime the alarm location(s) of the MPERS users do not have a Wi-Fi or GPS signal, requiring an agent of the PERS service center to rely on a limited number of historical IBC records to track down the alarm location as accurate as possible. Same location recognition and home location recognition avoids duplicated IBC records, which provides the PERS service center with the most effective historical IBC records, and also provides the last home timestamp, which informs a responder (e.g., family member or emergency personnel) the MPERS user's proximity to home. That is, certain embodiments of MPERS devices avoid the redundancy of IBC records, thus saving device memory for storing the IBC records, and enabling reporting historical locations to the service center more effectively for the IBC location.

Having summarized certain features and benefits of an MPERS device of the present disclosure, reference will now be made in detail to the description of an MPERS device as illustrated in the drawings. While an MPERS device will be described in connection with these drawings, there is no intent to limit the MPERS device to the embodiment or embodiments disclosed herein. For instance, though the MPERS devices described herein use nearby external devices configured as Wi-Fi AP's for relative, or home/same location, recognition, the same or similar functionality may be achieved by detecting the wireless signals of other external devices, including Bluetooth devices and/or some sensors or IoT (Internet of Things) devices having accessible wireless identifying information. As another example, though the MPERS devices described herein use the home/same location recognition to skip a GPS fix acquisition/operation and enable an informative alert (and/or response to the alert), some embodiments may also be used to trigger other actions, including the opening of an electronic door lock (e.g., to allow the device user to get in, to enable entry of emergency personnel, etc.), and/or to activate certain devices (including software and/or hardware), including turning on lights or other appliances, including a television (TV) or some application on a personal computer (PC) or tablet, or even turn on the AC or heater (e.g., if a fall is detected and the user is incapacitated, the user is determined to be in the home, and temperatures drop a defined amount, then the heater may be turned on or settings adjusted). Also, though described herein using MPERS devices in situations where a user may have fallen or suffered some other medical issue, including wandering episodes in dementia patients or some other medical event, this is one illustrative type of application, and some embodiments may use other types of wearable devices or mobile devices that are not wearable in other applications, including devices for telephony, gaming, among other applications and/or devices. For instance, any battery-powered location aware device can utilize the wireless locating functionality of the MPERS device to save power and improve operational time. Similarly, cell phones may utilize such functionality to save power when a user is in the same location, or alert devices may use this functionality to provide users home proximity. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents consistent with the disclosure as defined by the appended claims. Further, it should be appreciated in the context of the present disclosure that the claims are not necessarily limited to the particular embodiments set out in the description.

Figure 1:
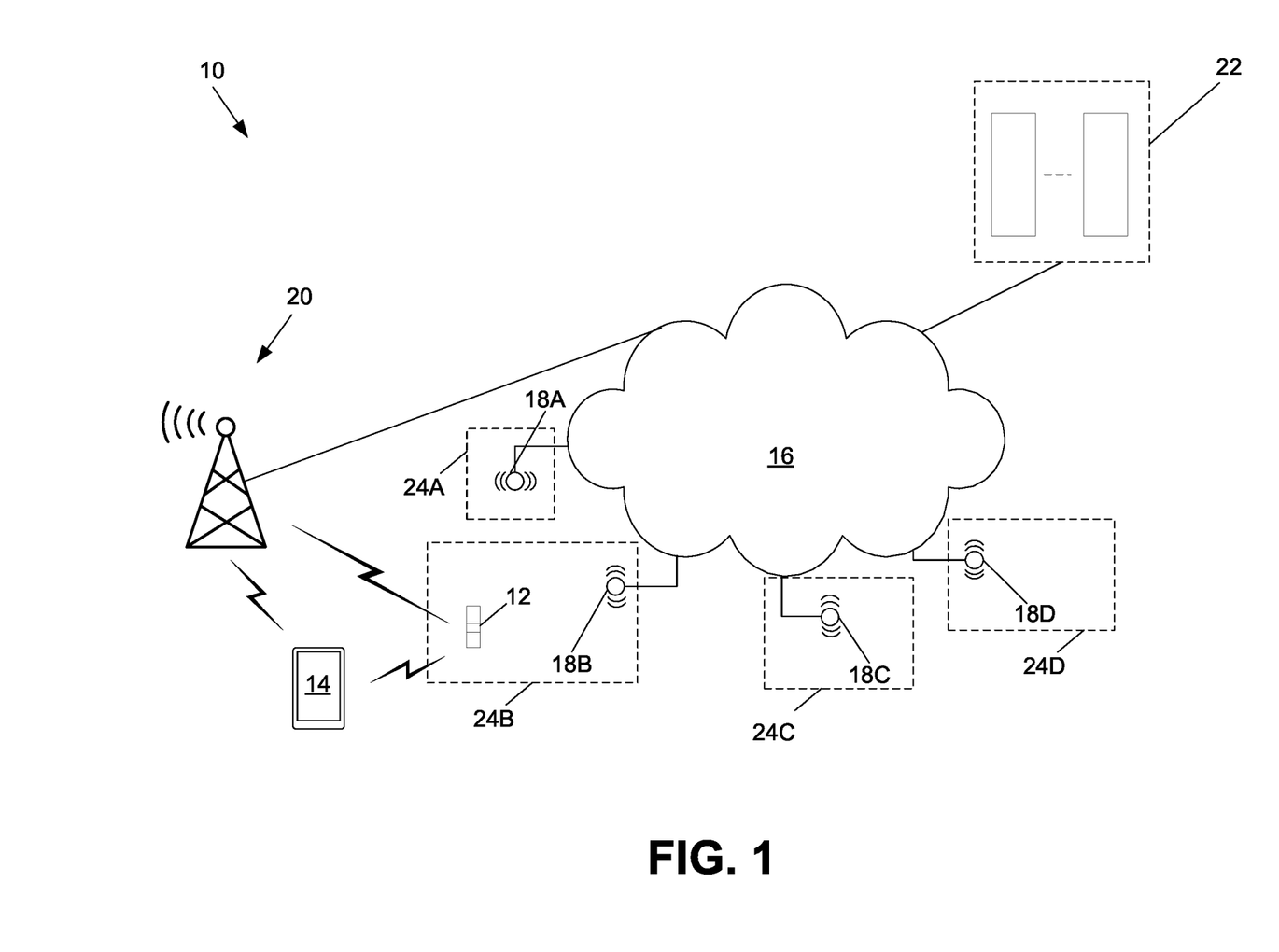
FIG. 1 is a schematic diagram that illustrates an example environment in which a mobile, personal emergency response system (MPERS) device is used, in accordance with an embodiment of the invention.

Referring now to FIG. 1, shown is an example environment 10 in which certain embodiments of an MPERS device may be implemented. It should be appreciated by one having ordinary skill in the art in the context of the present disclosure that the environment 10 is one example among many, and that some embodiments of an MPERS device may be used in environments with fewer, greater, and/or different components than those depicted in FIG. 1. The environment 10 comprises a plurality of devices that enable communication of information throughout one or more networks. The depicted environment 10 comprises an MPERS device 12, an electronics device 14, a wide area network 16 (e.g., the Internet), plural external devices 18 (i.e., external to the MPERS device 12), a cellular network 20, and one or more devices (e.g., computing and/or communication devices) of a PERS (service) facility 22, some of which are used by agents (personnel) of the facility to assist users of the MPERS device 12.

Figure 2:
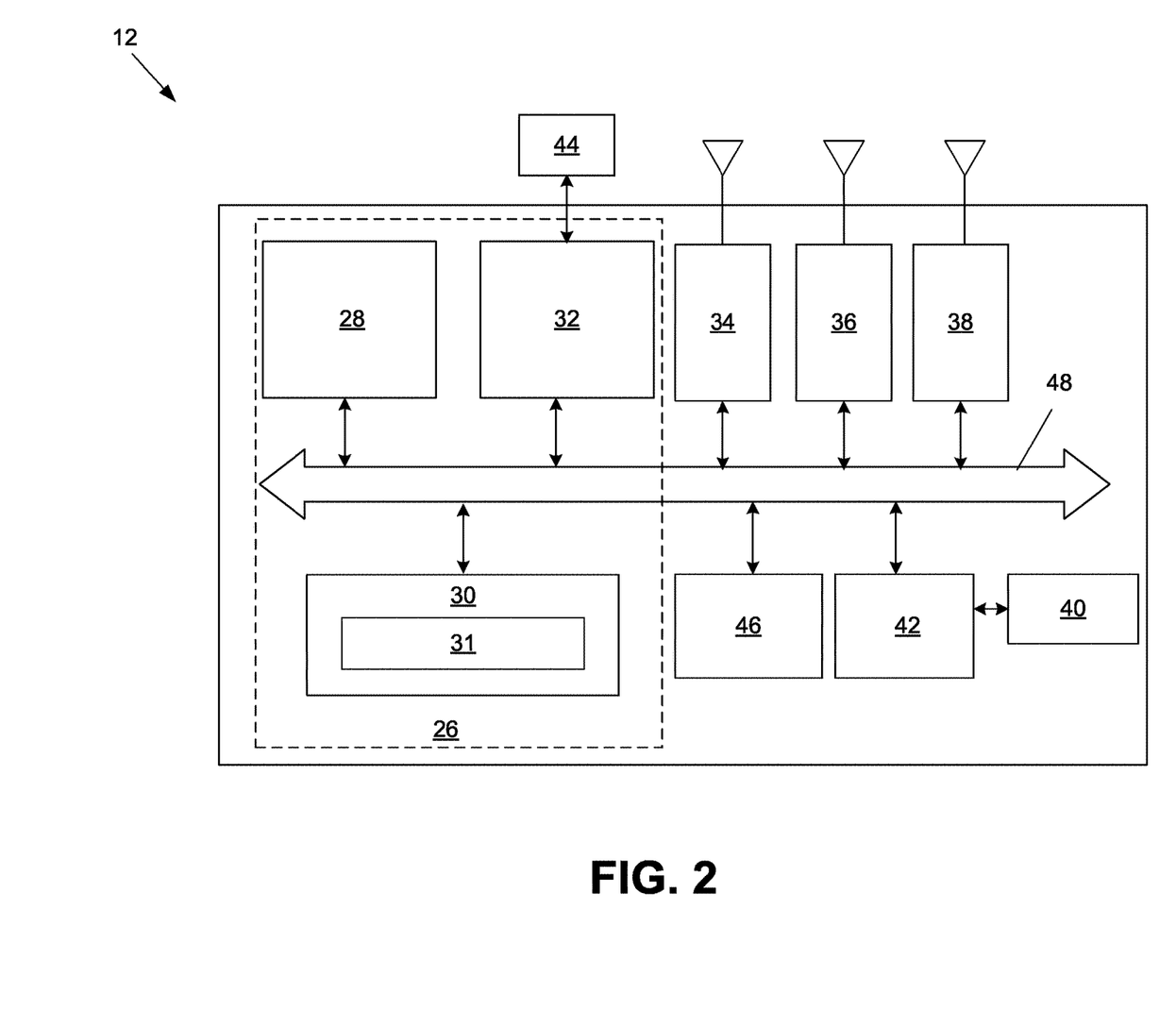
FIG. 2 is a block diagram that illustrates an example MPERS device, in accordance with an embodiment of the invention.

The MPERS device 12, as described further in association with FIG. 2, is typically worn by the user (e.g., around the wrist in the form of a watch, strap, or band-like accessory, suspended from the user's neck as a pendant, attached to an article of clothing, or embedded within the user), and in one embodiment, comprises one or more processors, a wireless scanning module, a position location module (e.g., GPS module), an optional cellular module, and a plurality of sensors, among other components described below. The MPERS device 12 may further comprise fall detection software or other emergency assist software that receives an indication of an emergency event (e.g., either detected autonomously based on the use of one or more sensors or via a user depressing a button or other input) and responsively triggers an action at (e.g., sends an alert to) one or more devices of the PERS facility 22 or other devices (e.g., to a family member, friend, or other caregiver). An agent at the PERS facility 22 can assist the user by contacting, on behalf of the user, emergency personnel or other designated caregivers. Communication between the MPERS device 12 and the PERS facility 22 may be achieved via one or a combination of the cellular network 20, the wide area 16, and/or other networks. In one embodiment, the MPERS device 12 communicates with the PERS facility 22 directly (e.g., using cellular modem functionality) or via an intervening communication through the electronics device 14.

The electronics device 14 may be embodied as a smartphone, mobile phone, cellular phone, pager, stand-alone image capture device (e.g., camera), laptop, tablet, workstation, smart glass (e.g., Google Glass™), virtual reality device, augmented reality device, among other handheld and portable computing/communication devices. In some embodiments, the electronics device 14 is not necessarily readily portable or even portable. For instance, the electronics device 14 may be a home appliance, including a refrigerator, microwave, oven, pillbox, home monitor, stand-alone home virtual assistant device, one or more of which may be communicatively coupled to the MPERS device 12 and/or the PERS facility 22 via one or more networks (e.g., through a home Internet connection or telephony network). In some embodiments, the electronics device 14 may be a vehicle appliance (e.g., the automobile navigation system or communication system). In the depicted embodiment of FIG. 1, the electronics device 14 is embodied as a smartphone, though it should be appreciated that the electronics device 14 may take the form of other types of devices including those described above, and is thus shown as a smartphone for illustration.

The environment 10 also includes plural external devices 18 (e.g., 18A-18D). In one embodiment, the external devices 18 are configured as wireless fidelity (Wi-Fi) access points, which provide a wireless local area network (WLAN) that projects wireless (Wi-Fi) signals for detection and/or reception within a given range to the wearable device 12 and/or electronics device 14. The external device 18 is connected to the wide area network 16 (e.g., via a router, switch, or hub using an Ethernet connection). One or more of the external devices 18 may be located in various facilities 24 (e.g., 24A-24D), including residential homes, businesses, government institutions, among other types of facilities. The external devices 18 may each store various information, including one or more types of identifiers (e.g., media access control (MAC), SSID, etc.). During a scan by the MPERS device 12, one (e.g., MAC address) or more of the information may be used (after a comparison with prior recorded data and based on a threshold match) to recognize a relative location (e.g., a same or home location). Though described herein as embodied as a Wi-Fi access point, in some embodiments, the external device 18 may be embodied as other types of devices, including Bluetooth-enabled devices, optical coding devices, among other types of devices (including the various types of electronic devices 14) that can be used by the MPERs device 12 for recognition of a same or home location based on their projected wireless signals and corresponding information (e.g., identifiers).

The cellular network 20 may include the necessary infrastructure to enable cellular communications by the electronics device 14 and/or the MPERS device 12. There are a number of different digital cellular technologies suitable for use in the cellular network 20, including: GSM, CPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (DEN), among others.

The wide area network 16 may comprise one or a plurality of networks that in whole or in part comprise the Internet. The electronics device 14 and/or MPERS device 12 may access one or more devices of the PERS facility 22 via the Internet 16 and/or via one or more other networks including PSTN (Public Switched Telephone Networks), POTS, Integrated Services Digital Network (ISDN) Ethernet, Fiber, DSL/ADSL, WiFi, Zigbee, BT, BTLE, among others.

The PERS facility 22 comprises one or more devices coupled to the wide area network 16 and/or the cellular network 20, including one or more computing devices networked together, including an application server(s) and data storage. The PERS facility 22 may serve as a cloud computing environment (or other server network) for the electronics device 14 and/or wearable device 12. In one embodiment, the PERS facility 22 serves as a call or PERS service center, receiving alerts or, in general, communications from the MPERS device 12 and/or electronics device 14 and providing service agents to communicate with the users of the devices 12 and/or 14 to assist in his or her emergency. In some embodiments, alerts may be used to trigger device action at the PERS facility 22 or elsewhere, including auto-dialing (e.g., to communicate with PERS agents, emergency personnel or family members), remote door unlock (e.g., signals to the user's residence to unlock the door for emergency personnel), remote light activation (e.g., activating an outdoor front light on and off to assist emergency personnel in finding the residence where the user is having an issue), among other device actions. Note that in some embodiments, the MPERS 12 and/or electronics device 14 may communicate an alert (e.g., formatted as a text message or voice message or email) to other devices of individuals or entities that are designated (e.g., by the user) as recipients of the alert (i.e., that will assist the subject in the case of a fall or other emergency).

Having described an example environment 10 in which certain embodiments of an MPERS device 12 may be used, attention is now directed to FIG. 2, which illustrates an embodiment of an MPERS device 12. It should be appreciated by one having ordinary skill in the art, in the context of the present disclosure, that the architecture depicted in FIG. 2 is one illustrative embodiment, and that in some embodiments, fewer, additional, and/or different components may be used to achieve the wireless locating functionality of the MPERS device 12. In the depicted embodiment, the MPERS device 12 comprises a microcontroller 26 having one or more processors 28 (one shown), memory (e.g., FLASH memory) 30, and I/O interfaces 32. The MPERS device 12 also comprises a GPS module 34, Wi-Fi module 36, and an optional cellular module 38. The MPERS device 12 further comprises a battery 40 and a charger/gauge chip (CHARGER) 42. The MPERS device 12 also comprises a user interface (UI) 44, and in some embodiments, one or more sensors 46. The aforementioned components are all coupled over one or more data busses, such as data bus 48.

The microcontroller 26 comprises a hardware device for executing software/firmware, particularly that stored in memory 30. The microcontroller 26 comprises one or more processors 28, each of which may include any custom made or commercially available processor, a central processing unit (CPU), a semiconductor based microprocessor (in the form of a microchip or chip set), a macroprocessor, or generally any device for executing firmware/software instructions. The microcontroller 26 provides for management and control of the MPERS device 12. Though a microcontroller 26 is described, it should be appreciated by one having ordinary skill in the art in the context of the present disclosure that other processor configurations and/or arrangement of components for like-functionality may be used in some embodiments, including systems on a chip among other arrangements, and hence are contemplated to be within the scope of the disclosure.

The memory 30 can include any one or a combination of volatile memory elements (e.g., random access memory (RAM, such as DRAM, SRAM, SDRAM, etc.)) and non-volatile memory elements (e.g., ROM, Flash, solid state, EPROM, EEPROM, etc.). In some embodiments, additional memory may be coupled to the data bus 48. Moreover, the memory 30 may incorporate electronic, magnetic, and/or other types of storage media. The memory 30 may be used to store sensor data and information about previously scanned external devices 18, the information including one or any combination of device identification (e.g., MAC address, SSID), signal strength (e.g., RSSI), among other identifier and/or signal strength information. The memory 30 may also store position location information (e.g., GPS coordinates), such as from operations of the GPS module 34, and associate the information from a wireless scan of nearby wireless devices to a designated location (e.g., home or same location). The memory 30 may further include executable code in the form application software and/or firmware (app 31) that controls and manages the wireless scanning, information recording (IBC records) and memory management (e.g., FIFO operations, time stamps, etc.), comparisons to historical data, alert delivery format and delivery methods, and location recognition/determination, as described further below. In some embodiments, the memory 30 may also comprise a fall detection algorithm and/or other behavioral and/or user state algorithms that use various sensors (e.g., accelerometers, air pressure sensors, etc.) to detect movements or patterns of movements of the torso and/or limbs, and optionally other information (e.g., contextual information), to make a determination of a fall event or other emergency events. For instance, accelerometer input may be single or double integrated to obtain respective velocity or body orientation/position (e.g., providing an inference that the user has fallen), or a change in air pressure in combination with the accelerometer information may be used to determine a rapid drop in height (e.g., a fall). In some embodiments, the memory 30 may include an operating system and in some embodiments may be omitted. The memory 30 may also include user data, including weight, height, age, gender, goals, body mass index (BMI). The user data may also include historical data relating past recorded data to prior contexts, including fall history, and/or contact information (e.g., phone numbers) in the case of a fall event. In some embodiments, all or a portion of the user data may be stored elsewhere (e.g., at the electronics device 14 and/or a device(s) of the PERS facility 22).

The I/O interfaces 32 comprise a plurality of (serial) pins, including serial ports (e.g., UARTS) for the input and/or output of data. In one embodiment, the I/O interfaces 32 are connected to the user interface 44, though in some embodiments, the user interfaces 44 may be coupled directly to the data bus 48.

The GPS module 34 comprises a GPS receiver including one or more antennas for receiving satellite data and computing a geographical location of the MPERS device 12. Though described as a GPS receiver, the GPS module 34 may be configured according to one or more global navigation satellite system (GNSS) capabilities, including GPS, GLONASS, etc. In some embodiments, the GNSS receiver functionality may be replaced with, or augmented by, other position location determination functionality, such as cell tower triangulation, dead-reckoning (e.g., using inertial sensors), among others. A position location module, as used herein, may be embodied as the GPS module 34 (e.g., GPS receiver), a GNSS module (e.g., GNSS receiver), or a module comprising triangulation and/or other position location functionality.

The Wi-Fi module 36 enables the detection of wireless signals from nearby external devices 18. For instance, the Wi-Fi module 36 comprises one or more antennas and known transceiver circuitry that regularly (e.g., every five (5) minutes) scans the environment for wireless signals emitted from the external devices 18, recording information (e.g., identifiers) for all or a predetermined quantity of external devices 18 (e.g., those with the greatest signal strength, such as the top two or top five). Though described as a Wi-Fi module 36 for detecting Wi-Fi signals, the Wi-Fi module 36 may be configured to scan for detection of, and information extraction from, other and/or additional types of wireless signals, including Bluetooth signals, wireless signals of other protocols, standards, and/or specifications, and/or wireless signals from other frequency ranges of the electromagnetic frequency spectrum (e.g., wireless signals coded via light, sound, etc.). A wireless communications module, as used herein, may be embodied as the Wi-Fi module 36 and/or other modules for providing the aforementioned scan/detection functionality using signals of other types.

The cellular module 38 enables cellular communications between the MPERS device 12 and other devices, including electronic devices 14 and/or devices of the PERS facility 22. The cellular modules 38 may comprise a cellular modem and one or more antennas that enable communications using one or any combination of cellular technologies, including GSM, CDMA, WCDMA, among others. The cellular module 38 communicates an alert when the user has depressed an alarm or an emergency event has been autonomously discovered, and may also receive communications from an agent of the PERS facility 22 (e.g., confirming the emergency event). In some embodiments, the cellular module 38 may be omitted, and communications between the MPERS device 12 and one or more devices of the PERS facility 22 are achieved via an intermediary device (e.g., the electronics device 14) or via the Internet. For instance, telephony and/or data transfers may be achieved using a Wi-Fi or Bluetooth access point (among other technologies) that is connected to the Internet in lieu of the cellular modem 38 to achieve these functions.

The MPERS device 12 further comprises a battery 40 (or other power source) and a charging/gauge chip 42 to enable a re-charging of the battery 40.

The MPERS device 12 also comprises a user interface 44. In one embodiment, the user interface 44 may be a button that the user presses when in need of assistance, the button press detected by the microcontroller 26, which in turn communicates an alert, in one embodiment, via the cellular module 38. In some embodiments, the user interface 44 may additionally, or alternatively, comprise a touch-type display screen and/or microphone, where user inputs (e.g., commands) are delivered via touch-input, audibly, and/or via gesture and communications presented via text, audio and/or video, graphics, and/or via haptic feedback. For instance, the display screen may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), retina or haptic-based technology, or virtual/augmented reality technology. In some embodiments, the user interface 44 may comprise light components (e.g., LEDs), haptic feedback components (e.g., vibratory motors), among other devices or components for enabling further and/or other user interaction with the MPERS device 12.

In some embodiments, the MPERS device 12 comprises one or more sensors 46. The sensors 46 may comprise an air pressure sensor and a single or multi-axis accelerometer (e.g., using piezoelectric, piezoresistive or capacitive technology in a microelectromechanical system (MEMS) infrastructure), respectively, for the detection of, for instance, falls. In some embodiments, the sensors 46 may further, or alternatively, include functionality for the detection and measurement of a plurality of physiological and behavioral parameters. For instance, typical physiological parameters include heart rate, heart rate variability, heart rate recovery, blood flow rate, activity level, muscle activity in addition to arm direction, including core movement, body orientation/position, power, speed, acceleration, etc.), muscle tension, blood volume, blood pressure, blood oxygen saturation, respiratory rate, perspiration, skin temperature, electrodermal activity (skin conductance response), body weight, and body composition (e.g., body mass index or BMI), articulator movements (especially during speech). Typical behavioral parameters or activities including walking, running, cycling, and/or other activities, including shopping, walking a dog, working in the garden, sports activities, browsing internet, watching TV, typing, etc.). One of the sensors 46 may be embodied as an inertial sensor (e.g., gyroscopes) and/or magnetometers. The sensors 46 may also include flex and/or force sensors (e.g., using variable resistance), electromyographic sensors, electrocardiographic sensors (e.g., EKG, ECG), magnetic sensors, photoplethysmographic (PPG) sensors, bio-impedance sensors, infrared proximity sensors, acoustic/ultrasonic/audio sensors, a strain gauge, galvanic skin/sweat sensors, pH sensors, temperature sensors, and photocells. The sensors 46 may include other and/or additional types of sensors for the detection of environmental parameters and/or conditions, for instance, barometric pressure, humidity, outdoor temperature, pollution, noise level, light level, etc. One or more of these sensed environmental parameters/conditions may be influential in the determination of the state or condition of the user. In some embodiments, the sensors 46 may be embodied as an image capture device comprising an optical sensor (e.g., a charged coupled device (CCD) or a complementary metal-oxide semiconductor (CMOS) optical sensor). For instance, the image capture device may be used to detect various physiological parameters of a user, including blood pressure based on remote photoplethysmography (PPG). In some embodiments, all or a portion of the sensor functionality may be omitted, or performed all or in part at another device (e.g., the electronics device 14) and communicated to the PERS facility 22 in conjunction with (or separate from) the alert.

The software/firmware (app 31) in memory 30 comprises a source program, executable program (object code), script, or any other entity comprising a set of instructions/executable code to be run (performed). When a source program, then the program may be translated via a compiler, assembler, interpreter, or the like, so as to operate properly in connection with the operating system. Furthermore, the software/firmware can be written as (a) an object oriented programming language, which has classes of data and methods, or (b) a procedure programming language, which has routines, subroutines, and/or functions, for example but not limited to, C, C++, Python, Java, among others. The software/firmware may be embodied in a computer program product, which may be a non-transitory computer readable medium or other medium.

When certain embodiments of the MPERS device 12 are implemented at least in part with software/firmware (e.g., app 31), it should be noted that the software/firmware can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the MPERS device 12 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

It should be appreciated by one having ordinary skill in the art, in the context of the present disclosure, that certain known components may be omitted for the sake of brevity and simplicity in illustration. For instance, in embodiments of an MPERS device 12 where sensors 46 are used, analog to digital (ADC) components may be used to convert the analog sensor data to digital data for processing by the microcontroller 26. Further, sensor signals may be conditioned by digital and/or analog filtering and/or signal processing devices and/or software/firmware, as would be understood by one having ordinary skill in the art in the context of the present disclosure.

Having described an example MPERS device 12 and its corresponding components, further description follows below on an example operation of the MPERS device 12 under the management and control of the app 31 stored in memory 30 of the microcontroller 26. Digressing briefly, some MPERS devices (e.g., hybrid type devices) may employ GPS, Wi-Fi, and cell tower information for location during alarms. Sometimes the alarm location does not have a GPS or Wi-Fi signal, so historical location information may be very helpful to an agent or caregiver assisting a user in emergency circumstances. In one example operation, such MPERS devices execute a routine (e.g., every five (5) minutes) that performs a Wi-Fi scan and GPS Fix acquisition, and store the location information in memory. During an alarm, the historical location records are reported (together with the live location information) to a PERS facility to track down the best location. This process is called Intelligent Bread Crumbing (IBC). However, the GPS operation of the IBC routine consumes significant battery power. In contrast, certain embodiments of the MPERS device 12 minimize battery consumption of the device 12 by using the information from wireless signals of nearby external devices 18 (e.g., Wi-Fi APs and/or other wireless devices) for same location and home location recognition, enabling the MPERS device 12 to skip the position location fix (e.g., the GPS location operation) of the routine IBC algorithm.

Further, and digressing briefly once again, the PERS system uses the Wi-Fi location and GPS fix to locate the user, and the process of getting the GPS fix is both time and power consuming, especially when the user is at locations (e.g., inside buildings) without a GPS signal or a very weak GPS signal. According to the typical routine of the IBC algorithm, an MPERS device periodically (e.g., every five (5) minutes) scans the nearby Wi-Fi APs and gets the updated GPS fix to create a new IBC record. The GPS fix (if available) and information about some of the detected Wi-Fi AP's with strongest signal strength are stored in the IBC record buffer. At the time of an alarm (e.g., when the user presses a button or a fall is automatically detected), certain number of these historical IBC records are sent, together with the current IBC record, by the MPERS device to the PERS service center for the service agent to process and determine the most accurate location possible of the user. However, this IBC routine is power consuming. Further, because the duplicated same location IBC records overwrite the previous useful records, even with the help of the IBC algorithm, sometimes (e.g., when no live location information is available) the agents in the PERS service center may have a difficult time locating the device.

In contrast, certain embodiments of an MPERS device 12 make use of the fact that, since the MPERS device users may stay at the same location for an extended period of time, there is no need to get a GPS fix if the location is the same as the previously recorded location (recorded without access to an external database), nor is there a need to update the IBC record. During a periodical wireless (e.g., Wi-Fi) scanning, an embodiment of the MPERS device 12 detects the nearby external devices 18 (e.g., Wi-Fi APs) and uses information from all or some of the external devices (APs) (e.g., with the strongest signal strength) to compare with the stored/recorded information of Wi-Fi APs from the previous scanning. If a certain number (e.g., threshold, as defined/configured by the user or by the manufacturer of the MPERS device 12, such as based on demographics (e.g., population density)) of these APs matches those of the previous record (e.g., a threshold match of say, two MAC addresses), the same location is recognized and the GPS module 34 is not activated (i.e., no GPS operation is commenced) to get a fix. Further, the MPERS device 12 does not store a new IBC record in memory 30. Otherwise (i.e., if there is no threshold match), routine IBC operation is executed (with the GPS fix). Furthermore, certain embodiments of the MPERS device 12 enable the device to recognize a home location. For instance, when an alarm from the home is processed, a service agent of the PERS facility 22 sends a command (e.g., over the air) for the MPERS device 12 to perform a wireless (e.g., Wi-Fi) scan and to store information for the external devices 18 (e.g., the Wi-Fi APs, some of those with the strongest signal strength) for the home location in memory 30 of the device 12 (e.g., without accessing an external database). This process is referred to as a set home location. If later external devices 18 (e.g., Wi-Fi APs) are detected using an Intelligent Bread Crumbing (IBC) routine without GPS fix, the home location is recognized and as a result, a time stamp corresponding to the last home location is updated, and no GPS operation is executed, and no new IBC record is stored to the historical IBC buffer (in memory 30). The MPERS device 12 not only saves battery power, but also helps to track down the user during an alarm effectively when currently there is no GPS fix available. Since the MPERS device 12 avoids the redundancy of IBC records, it also saves space in memory 30 for storing the IBC records, and it reports historical locations to the PERS facility 22 more effectively for IBC location. Based on considerations of response time and power consumption, the MPERS device 12 may only send certain historical IBC records (e.g., in chronicle order) to the PERS facility 22. Without the same location recognition, the historical IBC buffer may be overflowed with all the duplicated location records if the user stays at the same place for a long period of time. Such records are not helpful for agents of the PERS facility 22 to do Bread Crumbing analysis and track down the best location when no current location information is available. Note also the reference to recording information from a scan for use in subsequent comparisons with a current scan without using an external database. In conventional systems, external databases are used to record APs from a Wi-Fi scan often with a corresponding GPS or other physical location. In contrast, the MPERS device 12 need not consume the power required to access an external database for accessing information from a past scan, as the information is recorded within memory 30 of the MPERS device 12, enabling a self-contained, power savings approach that also may improve response times.

In one example operation based on execution of the app 31 of the MPERS device 12, when the user device is around home and a set home location is triggered, on the next Wi-Fi scan, Wi-Fi APs will be stored as home Wi-Fi APs. The set home location may be triggered by an alarm and subsequent agent communication. In some embodiments, the set home location can be triggered in other ways (e.g., button push, cellular interface, Bluetooth, USB, UART etc.). Every Wi-Fi scan (e.g., every five (5) minutes, though other intervals may be used) thereafter will be matched against the home Wi-Fi APs. If the above-mentioned match comprises a threshold match, that means the MPERS device 12 is around home and the last home timestamp shall be updated along with location services stopped (e.g., power off or in power-save mode) until a predefined interval expires or Wi-Fi APs no longer match. The threshold for a match can be variable to adjust the sensitivity of the algorithm (of app 31). In one embodiment, Wi-Fi APs and GPS locations are only logged when there is no threshold match, creating a trail of unique location records (stored in memory 30 without the use of external memory or databases) and only one record of a home location even when present in the home location for an extended period of time. When the user possessing the MPERS device 12 goes outside the home, a Wi-Fi scan is triggered at regular intervals (e.g., every five (5) minutes). If there is a threshold match with a previous scan result, that will mean that the MPERS device 12 is located around the same location, and location services (e.g., GPS fix) can be stopped until a predefined interval expires or Wi-Fi APs no longer match.

Figure 3:
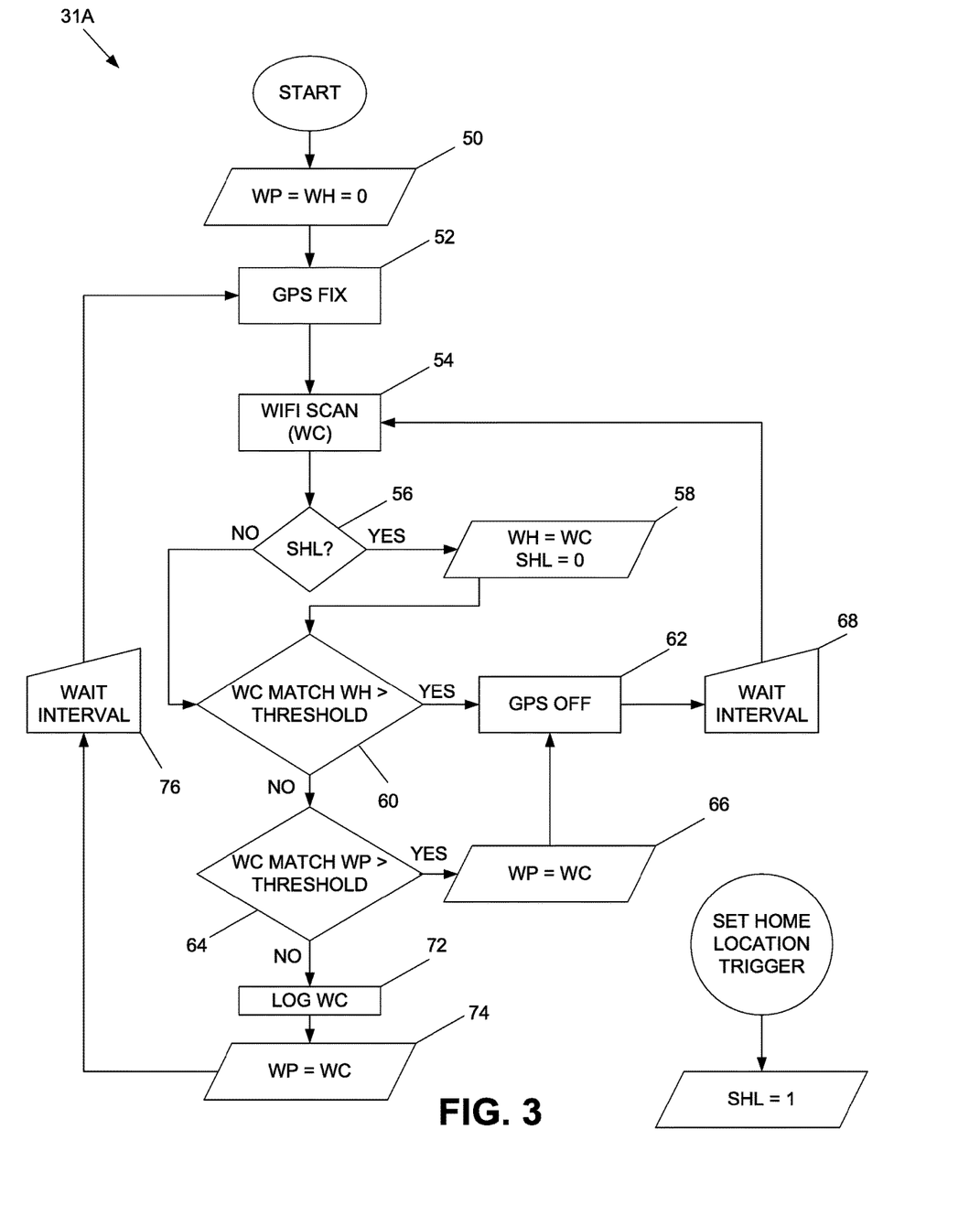
FIG. 3 is a flow diagram that illustrates an example method of operation for the MPERS device of FIG. 2, in accordance with an embodiment of the invention.

The immediately-above described process may be described in a flow diagram, as shown in FIG. 3 and denoted method 31A. After the start, an initialization of Wi-Fi APs from a previous scan (WP) and Wi-Fi APs from a home scan (WH) is set, or more simply, WP=WH=0 (50). A GPS fix is then implemented (52), followed by a Wi-Fi scan (WC, or Wi-Fi scan of the current detected APs) (54). The method 31A then determines whether a set home location (SHL) command is received (56). If yes, WH=WC and SHL=0 (58), followed by a determination of a threshold match between WC and WH (60). Note that in (56), a check is made to determine if the SHL flag has been set up (e.g., via a command communicated from the PERS facility), and if so, then the detected external devices (e.g., APs) from the scan (54) are associated as home location external devices, and the SHL flag (described below in association with the steps in the right hand side, bottom portion of FIG. 3) is cleared to avoid repeating the set home location step until needed (e.g., the home location has changed). Continuing, if there is a threshold match between WC and HW, position location services (e.g., GPS) is off (62), and after a wait interval (e.g., 5 minutes or another time, set by the manufacturer) (68), processing continues to (54). Referring again to (60), if there is not a threshold match between WC and WH, then in (64), a determination is made as to whether there is a threshold match between WC and WP (64). If so, the Wi-Fi APs from the previous scan (WP) are set equal to WC (66), and processing continues to (62). Otherwise (no to (64), WC is logged (72), WP=WC (74), and after a wait interval (74), processing continues to (52). Note on the bottom right had side of FIG. 3, in one embodiment, the set home location is initiated from the PERS facility (setting SHL=1), such that on the next wireless scan, the detected access points (or some sub-set thereof) are associated with the home location, after which information from subsequent scans are compared to a stored record corresponding to the set home location.

Though the above-description focuses on operations as managed and controlled by the app 31 running in the MPERS device 12, in some embodiments, functionality of the app 31 may be run in other and/or additional devices (e.g., electronics device 14) with the results communicated to the MPERS device 12, saving processing power on scanning and/or memory usage. Further, in some embodiments, the scanning and/or power saving intervals can be modified depending on usage. For instance, the scanning and/or power saving intervals can be dynamic depending on the battery level, such as to get optimum location coverage and/or battery operational time. In some embodiments, to further (or alternatively) reduce power consumption, in the absence of Wi-Fi or GPS signals, a back off scan algorithm may be implemented.

As set forth above, certain embodiments of an MPERS device 12 comprise multiple features to enable improvements in one or more of power savings, locating accuracy and speed of location determination, and memory space utilization through active wireless (e.g., Wi-Fi) scanning to detect the external devices (e.g., Wi-Fi APs) nearby, detection and local storage of a set of APs with the strongest signal strength, same location recognition (e.g., via Wi-Fi AP detection and comparison), set home location (e.g., via making use of the PERS system to set home location for the MPERS device 12), home location recognition (e.g., via Wi-Fi AP detection and comparison with the APs for the set home location), updates of the last home timestamp in the MPERS device at IBC routine Wi-Fi scans, skip position location (e.g., GPS) operations for a new fix when the same location or home location is recognized, skip storing IBC location records when the same location or home location is recognized, and/or report a non-duplicated historical IBC record and the last home time stamp to the service center (PERS facility) during an alarm (e.g., when button is pressed, fall is detected).

Figure 4:
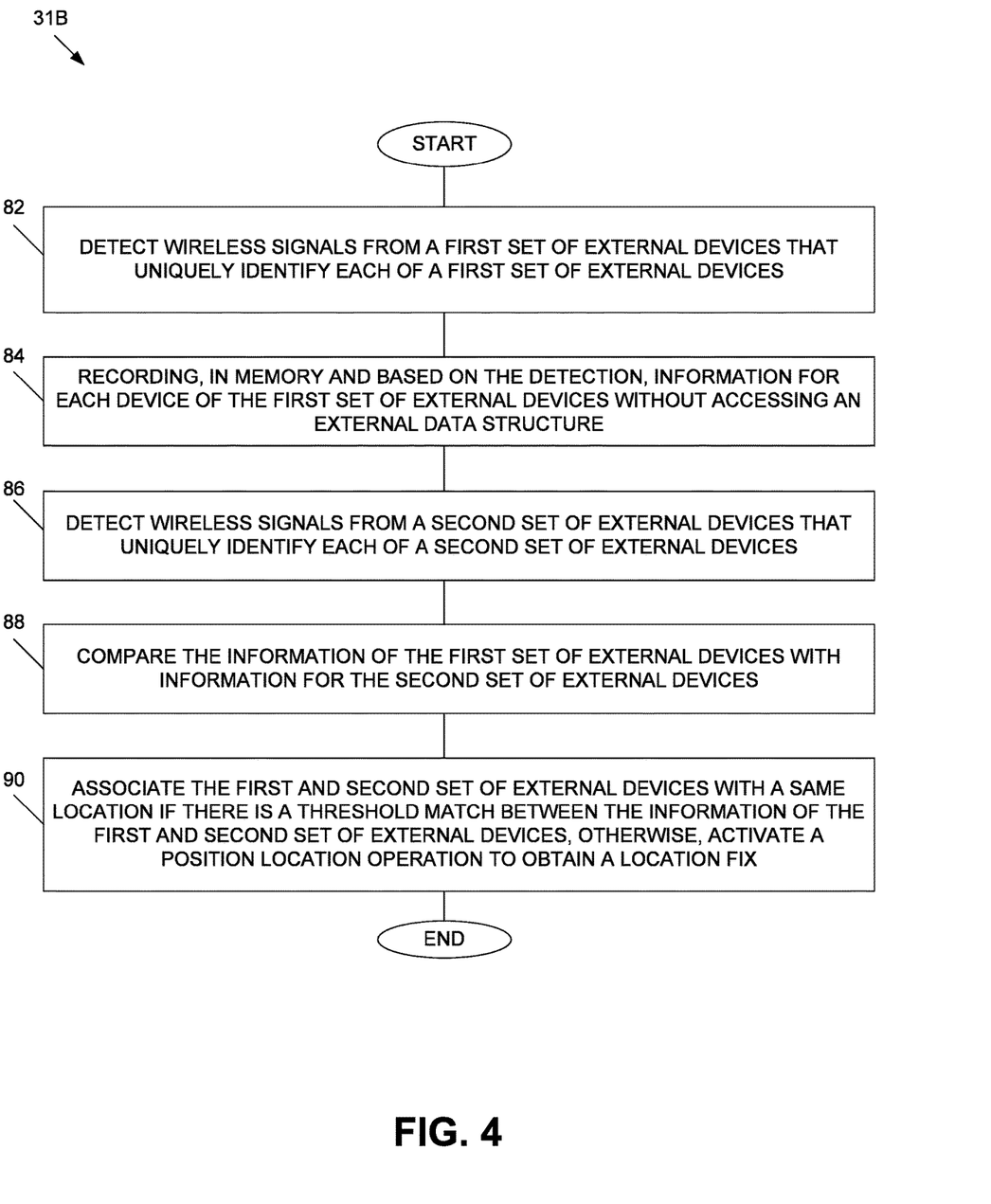
FIG. 4 is a flow diagram that illustrates an example wireless locating method, in accordance with an embodiment of the invention.

In view of the description above, it should be appreciated that one embodiment of a computer-implemented, wireless locating method, depicted in FIG. 4 and referred to as a method 31B (e.g., as executed by the MPERS device 12, and in particular, the app 31) and encompassed between start and end designations, comprises detecting wireless signals from a first set of external devices that uniquely identify each of the first set of external devices (82); recording, in memory and based on the detecting, information for each device of the first set of external devices without accessing an external data structure (84); detecting wireless signals from a second set of external devices that uniquely identify each of the second set of external devices (86); comparing the information of the first set of external devices with information for the second set of external devices (88); and associating the first and second set of external devices with a same location if there is a threshold match between the information of the first and second set of external devices, otherwise, activating a position location operation to obtain a location fix (90). In some embodiments, the method 31B further comprises triggering an action at another device based on transmittal of data comprising the same location or the location from the location fix. Note that the first and second set of external devices may or may not overlap. Further, it is noted that the wireless scans described herein are performed to associate external devices (within the range of the scan) using a unique identifier (e.g., serial number, MAC address) with a relative location for the MPERS device 12 (same location, home location), and do not include the actual physical address of the external devices or the use of actual physical address to determine the MPERS device. In one embodiment, the external devices may comprise access points, and the wireless signals comprise Wi-Fi signals. In some embodiments, the external devices comprise other types of devices that communicate wireless signals of other protocols, standards, specifications and/or in a range of the electromagnetic spectrum than is different than Wi-Fi. In other words, though Wi-Fi access points are emphasized herein, certain embodiments may use other external devices that may be uniquely and wirelessly identified (e.g., by the external device transmitting periodically a wireless signal that encodes its unique identifier (e.g., serial number, MAC address, etc.). The triggering of an action may include the sending of an alert that includes commands/instructions to activate a telephony auto-dialing function (e.g., to call emergency responders, PERS facility agents, etc.), activate lighting and/or audio hardware (e.g., emergency lights and/ or an audible alarm at a PERS facility, caregiver's residence, etc.), and/or prompt an email or text message on a device of an agent or caregiver. The triggering may also include the opening of doors (e.g., unlocking locks), among other devices.

Figure 5:
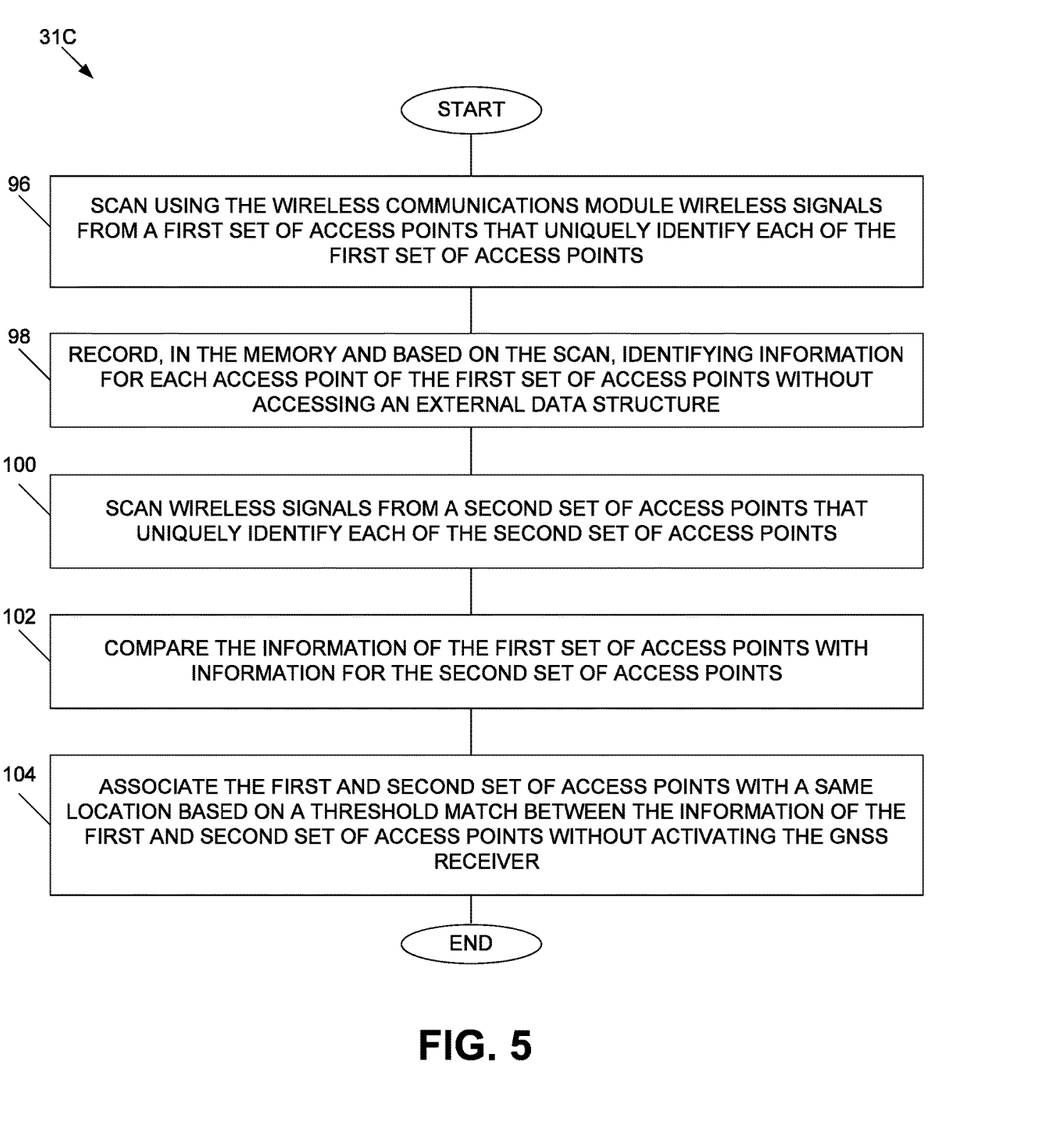
FIG. 5 is a flow diagram that illustrates another example wireless locating method, in accordance with an embodiment of the invention.

In view of the description above, it should be appreciated that yet another embodiment of a computer-implemented, wireless locating method, depicted in FIG. 5 and referred to as a method 31C (e.g., as executed by the MPERS device 12, and in particular, the app 31) and encompassed between start and end designations, comprises scanning using the wireless communications module wireless signals from a first set of access points that uniquely identify each of the first set of access points (96); recording, in the memory and based on the scan, identifying information for each access point of the first set of access points without accessing an external data structure (98); scanning wireless signals from a second set of access points that uniquely identify each of the second set of access points (100); comparing the information of the first set of access points with information for the second set of access points (102); associating the first and second set of access points with a same location based on a threshold match between the information of the first and second set of access points without activating a GNSS receiver (104); receiving an indication of an emergency event (106); and transmitting an alert to another device, based on the receiving of the indication, using the same location (108).

Figure 6:
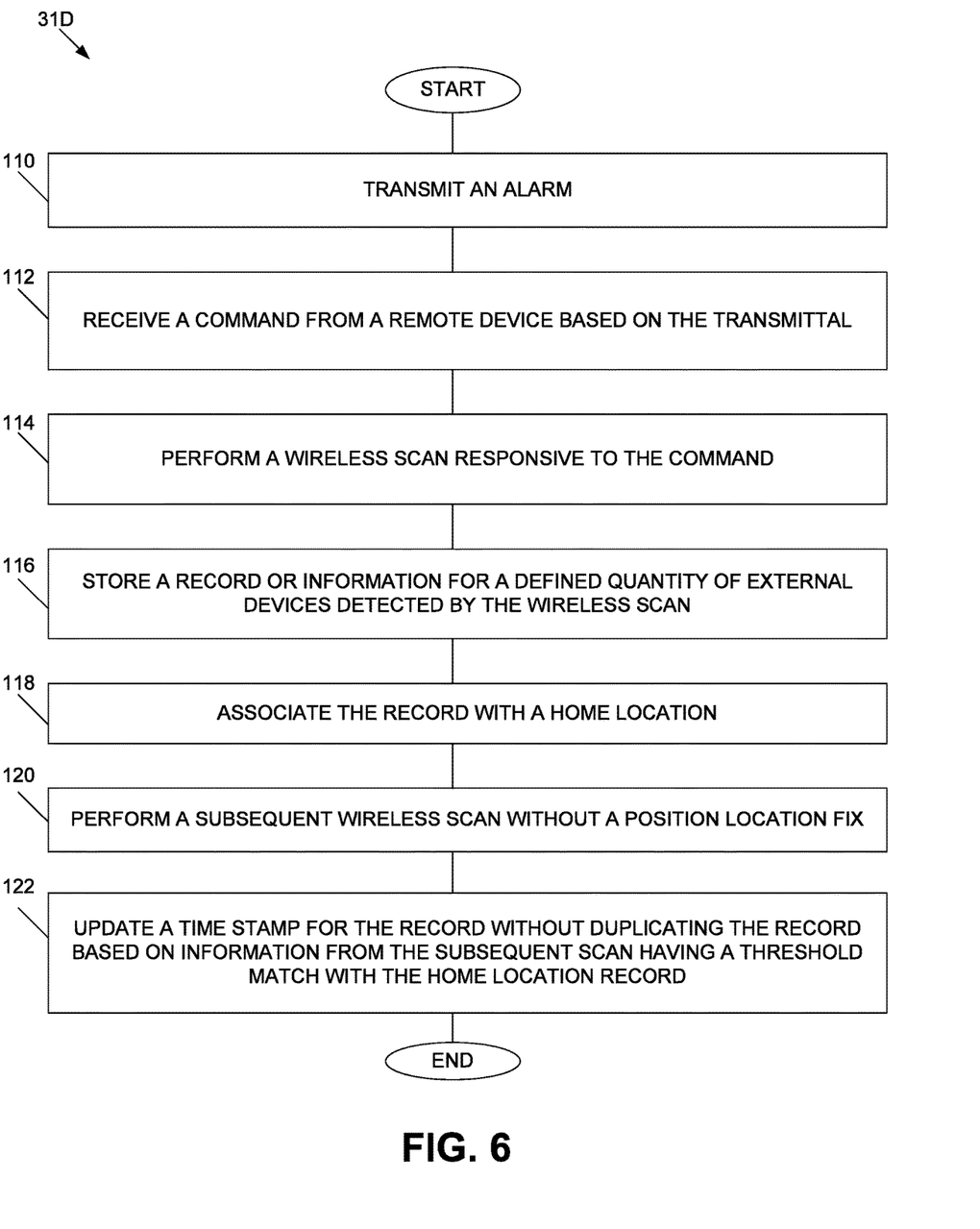
FIG. 6 is a flow diagram that illustrates an example process involving a set home location operation, in accordance with an embodiment of the invention.

In view of the description above, it should be appreciated that one embodiment of a computer-implemented, set home location method, depicted in FIG. 6 and referred to as a method 31D (e.g., as executed by the MPERS device 12, and in particular, the app 31) and encompassed between start and end designations, comprises transmitting an alarm (110); receiving a command from a remote device based on the transmittal (112); performing a wireless scan responsive to the command (114); storing a record or information for a defined quantity of external devices detected by the wireless scan (116); associating the record with a home location (118); performing a subsequent wireless scan without a position location fix (120); updating a time stamp for the record without duplicating the record based on information from the subsequent scan having a threshold match with the home location record (122).

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure.

In an embodiment, a claim to an apparatus, comprising: a memory comprising executable code; a position location module configured to obtain a location fix; a wireless communications module configured to receive data over a wireless medium; and a processor configured to run the executable code to: detect wireless signals from a first set of external devices that uniquely identify each of the first set of external devices; record, in the memory and based on the detection, information for each device of the first set of external devices without accessing an external data structure; detect wireless signals from a second set of external devices that uniquely identify each of the second set of external devices; compare the information of the first set of external devices with information for the second set of external devices; and associate the first and second set of external devices with a same location if there is a threshold match between the information of the first and second set of external devices, otherwise, activate the position location module to obtain the location fix.

In an embodiment, the apparatus of the previous claim wherein the processor is further configured to run the executable code to receive a command from a remote location based on a trigger, the trigger comprising transmittal of an alert.

In an embodiment, the apparatus of any one of the previous claims, wherein the processor is configured to run the executable code to further detect an emergency event for a user possessing the apparatus, and based on the detection, cause the transmittal of the alert.

In an embodiment, the apparatus of any one of the previous claims, wherein the alert further comprises the same location or the location from the location fix.

In an embodiment, the apparatus of any one of the previous claims, wherein the processor is configured to run the executable code to cause the wireless communications module to perform another wireless scan.

In an embodiment, the apparatus of any one of the previous claims, wherein the processor is configured to run the executable code to associate external devices detected from the another wireless scan to a home location.

In an embodiment, the apparatus of any one of the previous claims, wherein the association of the location of the apparatus to the home location is achieved without a location fix from the position location module.

In an embodiment, the apparatus of any one of the previous claims, wherein responsive to the threshold match, the processor is configured to run the executable code to further update a time stamp in memory corresponding to the information for the first set of external devices without populating the memory with the information for the second set of external devices.

In an embodiment, the apparatus of any one of the previous claims, wherein the position location module comprises a global navigation satellite systems (GNSS)-based receiver.

In an embodiment, the apparatus of any one of the previous claims, wherein the processor is configured to run the executable code to associate the first and second external devices without activating the location fix.

In an embodiment, the apparatus of any one of the previous claims, wherein the processor is configured trigger an action at another device using the same location or the location from the location fix by further causing a change in operation or state of the another device.

In an embodiment, the apparatus of any one of the previous claims, wherein the another device is located near the same location or near the location from the location fix.

In an embodiment, the apparatus of any one of the previous claims, wherein the another device is located at a remote facility.

In an embodiment, the apparatus of any one of the previous claims, further comprising a re-chargeable battery, wherein a primary source of power for operation of the apparatus is the re-chargeable battery.

In an embodiment, the apparatus of any one of the previous claims, further comprising a cellular module or the wireless communications module communicating through a device connected to the Internet, wherein said modules are configured to enable telephony and data transfer operations for the apparatus.

In an embodiment, the apparatus of any one of the previous claims, further comprising one or more sensors.

In an embodiment, the apparatus of any one of the previous claims, wherein the apparatus comprises a wearable device.

In an embodiment, a claim to a method implemented by a personal emergency response system (PERS) wearable device comprising one or more processors, a wireless communications module, a memory, and a global navigation satellite systems (GNSS) receiver, the method comprising: scanning using the wireless communications module wireless signals from a first set of access points that uniquely identify each of the first set of access points; recording, in the memory and based on the scan, identifying information for each access point of the first set of access points without accessing an external data structure; scanning wireless signals from a second set of access points that uniquely identify each of the second set of access points; comparing the information of the first set of access points with information for the second set of access points; and associating the first and second set of access points with a same location based on a threshold match between the information of the first and second set of access points without activating the GNSS receiver. In some embodiments, the apparatus may receive an indication of an emergency event, and transmit an alert to another device, based on the receiving of the indication, using the same location.

In an embodiment, a claim to the prior method, further comprising receiving a command from a remote facility based on the transmitting, performing an additional scan using the wireless communications module, and associating access points from the additional scan with a home location without activating the GNSS receiver.

In an embodiment, a claim to a non-transitory computer readable medium comprising executable code that, when executed by one or more processors of a mobile personal emergency response system (MPERS) device, causes the one or more processors to: scan wireless signals from a first set of access points that uniquely identify each of the first set of access points; record, in the computer readable medium and based on the scan, identifying information for each access point of the first set of access points without accessing an external data structure; scan wireless signals from a second set of access points that uniquely identify each of the second set of access points; compare the information of the first set of access points with information for the second set of access points; and associate the first and second set of access points with a same location based on a threshold match between the information of the first and second set of access points without activating global navigation satellite receiver functionality. In some embodiments, the computer readable medium may receive an indication of an emergency event and transmit an alert to another device, based on the receiving of the indication, using the same location.

Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:

1. An apparatus, comprising:
   a memory comprising executable code;
   a position location module configured to obtain a location fix;
   a wireless communications module configured to receive data over a wireless medium; and
   a processor configured to run the executable code to:
   receive a command to set a current location of the apparatus as a home location;
   in response to the command, detect wireless signals from a set of one or more external devices that uniquely identify each of the set of external devices;
   record in the memory, information for one or more of the devices of the set of external devices without accessing an external data structure; and
   associate in the memory the record with the home location.

2. The apparatus of claim 1, wherein the processor is further configured to run the executable code to receive the command from a remote location based on a trigger, the trigger comprising transmittal of an alert.

3. The apparatus of claim 1, wherein the processor is further configured to run the executable code to receive the command based on a trigger, the trigger comprising depression of a button.

4. An apparatus, comprising:
   a memory comprising executable code;
   a position location module configured to obtain a location fix;
   a wireless communications module configured to transmit and receive data over a wireless medium; and
   a processor configured to run the executable code to:
   detect wireless signals from a first set of external devices that uniquely identify each of the first set of external devices;
   record, in the memory and based on the detection, information for each device of the first set of external devices without accessing an external data structure;
   detect wireless signals from a second set of external devices that uniquely identify each of the second set of external devices;
   compare the information of the first set of external devices with information for the second set of external devices;
   associate the first and second set of external devices with a same location if there is a threshold match between the information of the first and second set of external devices, and
   activate an external device if the same location is confirmed.

5. The apparatus of claim 4, wherein the activation includes turning on an electronic appliance.

6. The apparatus of claim 4, wherein the activation includes turning on a light.

7. The apparatus of claim 4, wherein the processor is configured to run the executable code to trigger an action at another device using the same location, the triggering causing a change in operation or state of the other device.

8. The apparatus of claim 4, further comprising a cellular module or wireless communications module communicating through a device connected to the Internet, wherein said modules are configured to enable telephony and data transfer operations for the apparatus.

9. The apparatus of claim 4, further comprising one or more sensors.

10. The apparatus of claim 4, wherein the apparatus comprises a wearable device.

11. An apparatus, comprising:
    a memory comprising executable code;
    a position location module configured to obtain a location fix;
    a wireless communications module configured to receive data over a wireless medium; and
    a processor configured to run the executable code to:
    receive a command to set a current location of the apparatus as a home location;
    in response to the command, detect wireless signals from a set of one or more external devices that uniquely identify each of the set of external devices;
    record in the memory, information for one or more of the devices of the set of external devices without accessing an external data structure; and
    associate in the memory the record with the home location without using the location fix.

* * * * *